US010687973B2

(12) United States Patent
Chihlas

(10) Patent No.: US 10,687,973 B2
(45) Date of Patent: Jun. 23, 2020

(54) WALKING BOOTS AND METHODS OF MAKING THE SAME

(71) Applicant: Christopher Nicholas Chihlas, East Greenwich, RI (US)

(72) Inventor: Christopher Nicholas Chihlas, East Greenwich, RI (US)

( * ) Notice: Subject to any disclaimer, the term of this patent is extended or adjusted under 35 U.S.C. 154(b) by 0 days.

(21) Appl. No.: 16/457,378

(22) Filed: Jun. 28, 2019

(65) Prior Publication Data

US 2020/0015993 A1    Jan. 16, 2020

Related U.S. Application Data

(60) Provisional application No. 62/696,580, filed on Jul. 11, 2018.

(51) Int. Cl.
| | | |
|---|---|---|
| *A43B 13/00* | (2006.01) | |
| *A61F 5/01* | (2006.01) | |
| *A43B 7/14* | (2006.01) | |
| *A43B 3/02* | (2006.01) | |

(52) U.S. Cl.
CPC .......... *A61F 5/0195* (2013.01); *A43B 7/1405* (2013.01); *A61F 5/0111* (2013.01); *A43B 3/02* (2013.01)

(58) Field of Classification Search
CPC ....... A43B 7/1495; A43B 7/1405; A43B 3/02; A43B 7/20; A61F 5/0111; A61F 5/0195
USPC .......................................................... 36/103
See application file for complete search history.

(56) References Cited

U.S. PATENT DOCUMENTS

| | | | |
|---|---|---|---|
| 5,094,232 A * | 3/1992 | Harris | A43B 7/20 |
| | | | 602/16 |
| 5,250,021 A | 10/1993 | Chang | |
| 5,329,705 A | 7/1994 | Grim | |
| 5,368,551 A | 11/1994 | Zuckerman | |
| 5,571,077 A | 11/1996 | Klearman | |
| 6,361,514 B1 * | 3/2002 | Brown | A61F 5/0111 |
| | | | 128/882 |
| 6,648,843 B1 | 11/2003 | Marciano | |
| 8,021,317 B2 | 9/2011 | Arnold | |
| 2006/0229542 A1 * | 10/2006 | Sinreich | A61F 5/0111 |
| | | | 602/27 |

(Continued)

OTHER PUBLICATIONS

International Search Report in International Application No. PCT/US2019/039956, dated Nov. 25, 2019 (5 pages).

(Continued)

*Primary Examiner* — Timothy K Trieu
(74) *Attorney, Agent, or Firm* — Nixon Peabody LLP

(57) ABSTRACT

A boot includes a rigid outer shell including a base portion adjacent to a portion of a foot of a subject, a leg portion adjacent to a portion of a leg of the subject, and an ankle support portion integral with and coupling the base portion of the main body with the leg portion of the main body, the ankle portion of the main body being adjacent to two opposing sides of an ankle of the subject, the ankle support portion of the main body having one or more removable elements. A first one of the one or more removable elements, adjacent to a first one of the two opposing sides of the ankle, is configured to be removed from the rigid outer shell to aid in preventing contact between an incision area on the first side of the ankle of the subject and the rigid outer shell.

19 Claims, 14 Drawing Sheets

(56) References Cited

U.S. PATENT DOCUMENTS

| | | |
|---|---|---|
| 2010/0100020 A1 | 4/2010 | Fout |
| 2014/0128789 A1 | 5/2014 | Chen |
| 2014/0310993 A1 | 10/2014 | Hecker |
| 2015/0025431 A1 | 1/2015 | Liden |
| 2015/0075030 A1 | 3/2015 | Walborn |
| 2015/0351949 A1 | 12/2015 | Klutts |

OTHER PUBLICATIONS

Written Opinion in International Application No. PCT/US2019/039956, dated Nov. 25, 2019 (12 pages).

\* cited by examiner

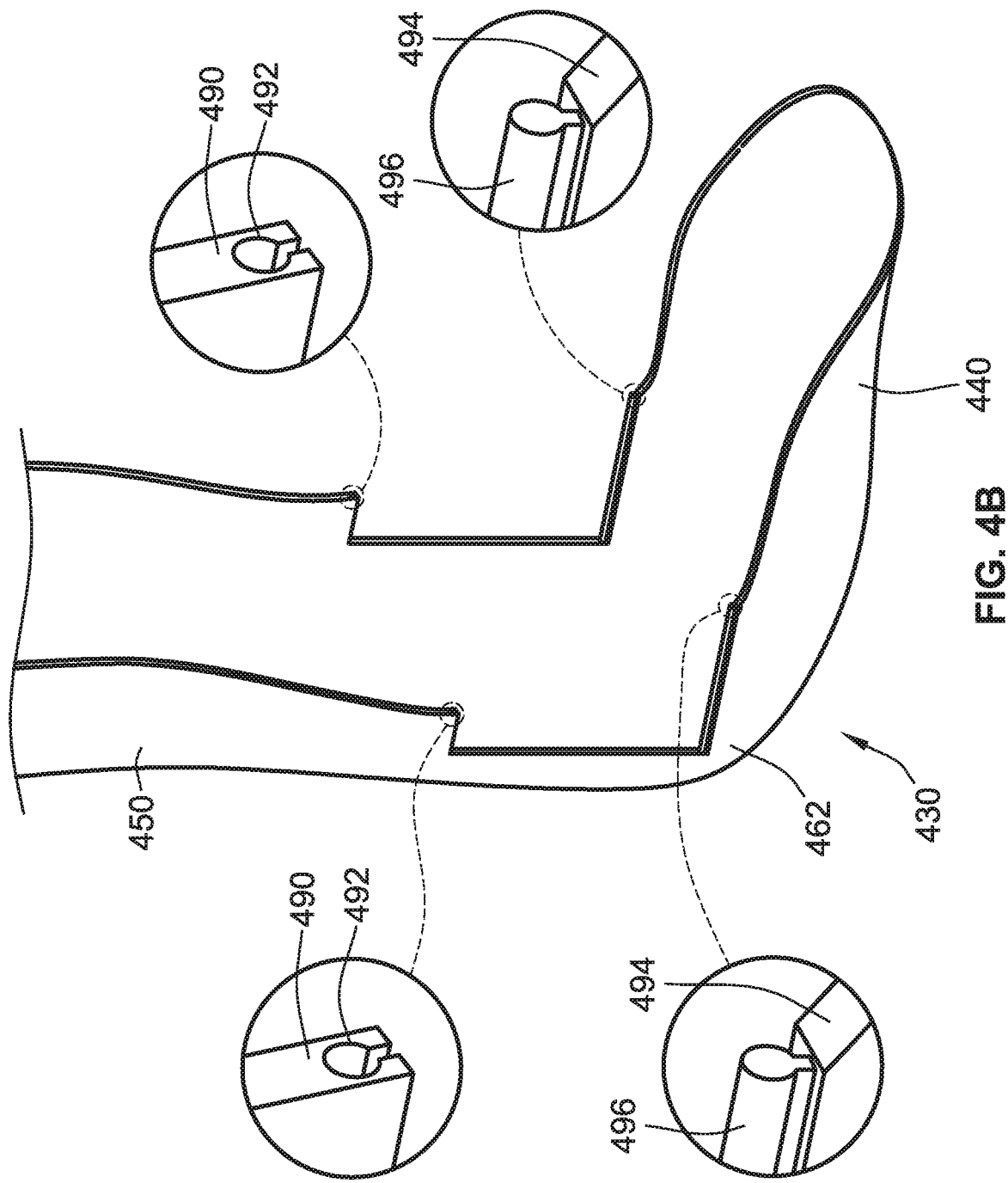

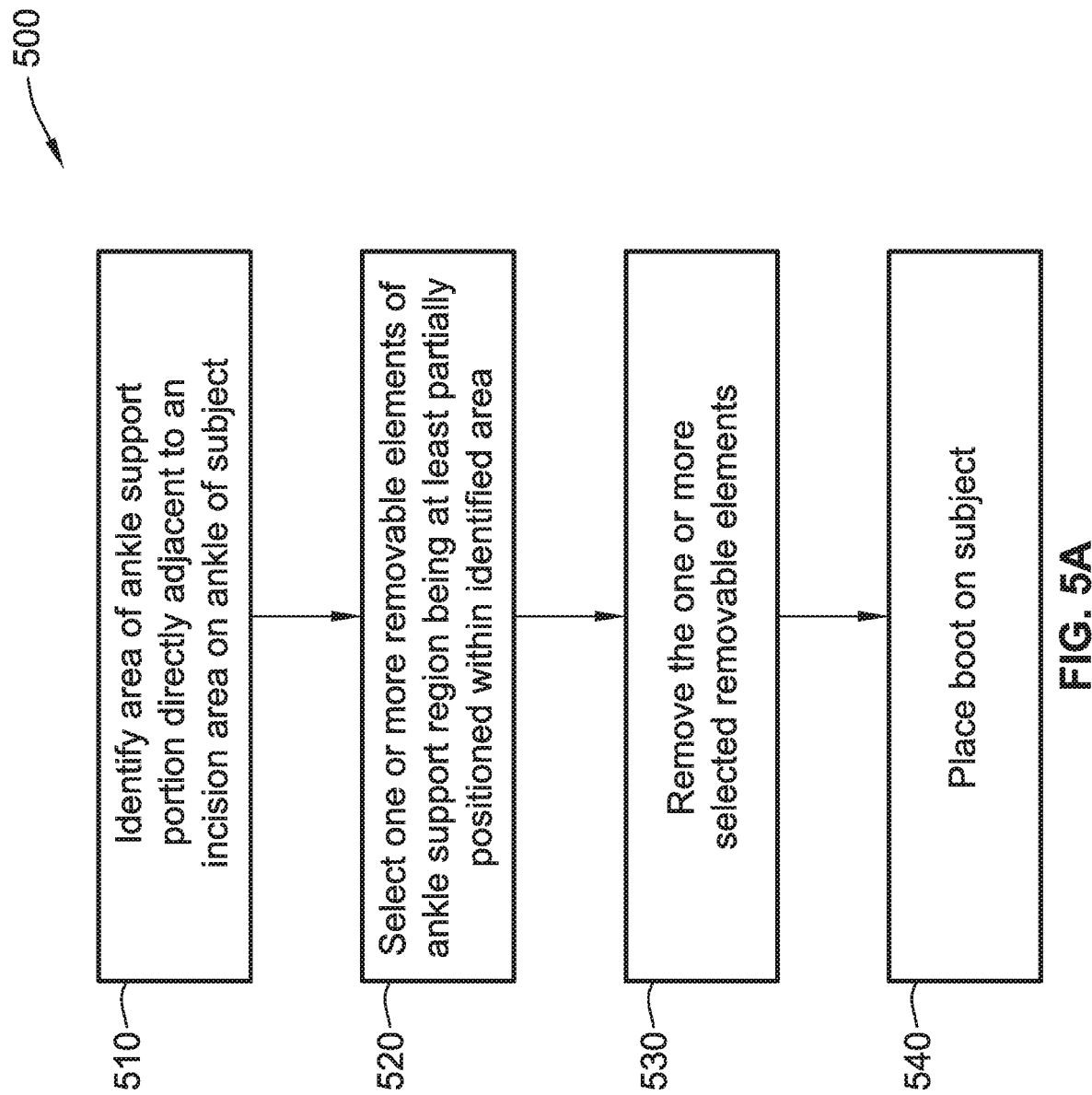

WALKING BOOTS AND METHODS OF MAKING THE SAME

CROSS-REFERENCE TO RELATED APPLICATIONS

This application claims the benefit of, and priority to, U.S. Provisional Application No. 62/696,580, filed on Jul. 11, 2018, which is hereby incorporated by reference herein in its entirety.

TECHNICAL FIELD

The present disclosure relates generally to walking boots. More specifically, the present disclosure relates to walking boots with one or more removable elements or openings and methods of making the same.

BACKGROUND

Ankle surgery often requires a physician to make one or more incisions on a patient's ankle. After surgery (e.g., one to two weeks after surgery), physicians often provide the patient with a walking boot (e.g., a controlled ankle motion or "CAM" walking boot) which immobilizes the ankle while permitting the patient to put weight on the injured ankle. The walking boot also aids in protecting the incision area from further injury. While these walking boots are often made from a rigid polymer material in order to provide sufficient mechanical support, this rigid polymer material can contact (e.g., directly or indirectly) the incision area on the ankle, which can cause the wearer of the walking boot pain/discomfort and/or adversely influence skin and/or incision healing due to, for example, the rigid polymer material rubbing on the incision and/or adjacent area of the incision. Moreover, such rubbing can cause the incision to break open (e.g., dehiscence), which can lead to infections and other negative complications. The present disclosure is directed to solving these and other problems.

SUMMARY

According to some implementations of the present disclosure, a boot includes a rigid outer shell including a main body having a base portion adjacent to a portion of a foot of a subject, a leg portion adjacent to a portion of a leg of the subject, and an ankle support portion integral with and coupling the base portion of the main body with the leg portion of the main body, the ankle portion of the main body being adjacent to two opposing sides of an ankle of the subject, the ankle support portion of the main body having one or more removable elements. A first one of the one or more removable elements, adjacent to a first one of the two opposing sides of the ankle, is configured to be removed from the rigid outer shell to aid in preventing contact between an incision area on the first side of the ankle of the subject and the rigid outer shell.

According to some implementations of the present disclosure, a boot includes a rigid outer shell including a main body having a base portion adjacent to a portion of a foot of a subject, a leg portion adjacent to a portion of a leg of the subject, and an ankle support portion integral with and coupling the base portion of the main body with the leg portion of the main body, the ankle portion of the main body being adjacent to two opposing sides of an ankle of the subject, the ankle support portion of the main body having an opening and one or more reinforcing members, wherein the opening in the ankle support portion aids in preventing contact between an incision area on the first side of the ankle of the subject and the rigid outer shell.

According to some implementations of the present disclosure, a method for making a walking boot includes identifying an area of an ankle support portion of a main body of a rigid outer shell of the boot that is directly adjacent to an incision area on an ankle of a subject when the boot is worn by the subject, selecting one or more removable elements of the ankle support portion being at least partially positioned within the identified area of the ankle support portion, and removing the one or more selected removable elements from the ankle support portion of the rigid outer shell, thereby aiding in preventing contact between the incision area on the ankle of the subject and the rigid outer shell when the boot is worn by the subject.

According to some implementations of the present disclosure, a boot includes a rigid outer shell including a main body having a base portion adjacent to a portion of a foot of a subject, a leg portion adjacent to a portion of a leg of the subject, and an ankle support portion integral with and coupling the base portion of the main body with the leg portion of the main body, the ankle portion of the main body being adjacent to two opposing sides of an ankle of the subject, the ankle support portion of the main body having an opening and a reinforcing portion adjacent to a portion of the opening, wherein the opening in the ankle support portion aids in preventing contact between an incision area on the first side of the ankle of the subject and the rigid outer shell.

According to some implementations of the present disclosure, a boot includes a rigid outer shell including a main body having a base portion configured to support a portion of a foot of a subject, a leg portion configured to support a portion of a leg of the subject, an ankle support portion integral with and coupling the base portion of the main body with the leg portion of the main body, the ankle portion of the main body being configured to support two opposing sides of an ankle of the subject, the ankle support portion including (i) an opening, (ii) a removable element disposed within the opening, and (iii) a bulged portion configured to receive an attachment portion of the removable element therein such that the removable element is removably coupled to the bulged portion, wherein responsive to decoupling of the removable element from the bulged portion, the opening in the ankle support portion aids in preventing contact between an incision area on the first side of the ankle of the subject and the rigid outer shell.

The above summary is not intended to represent each embodiment or every aspect of the present invention. Additional features and benefits of the present invention are apparent from the detailed description and figures set forth below.

BRIEF DESCRIPTION OF THE DRAWINGS

FIG. 4B is a perspective view of an upper track and a lower track of the main body of the rigid outer shell of FIG. 4A according to some implementations of the present disclosure;

FIG. 5A is a flow diagram of a method for making a walking boot according to some implementations of the present disclosure;

Figure 1A:
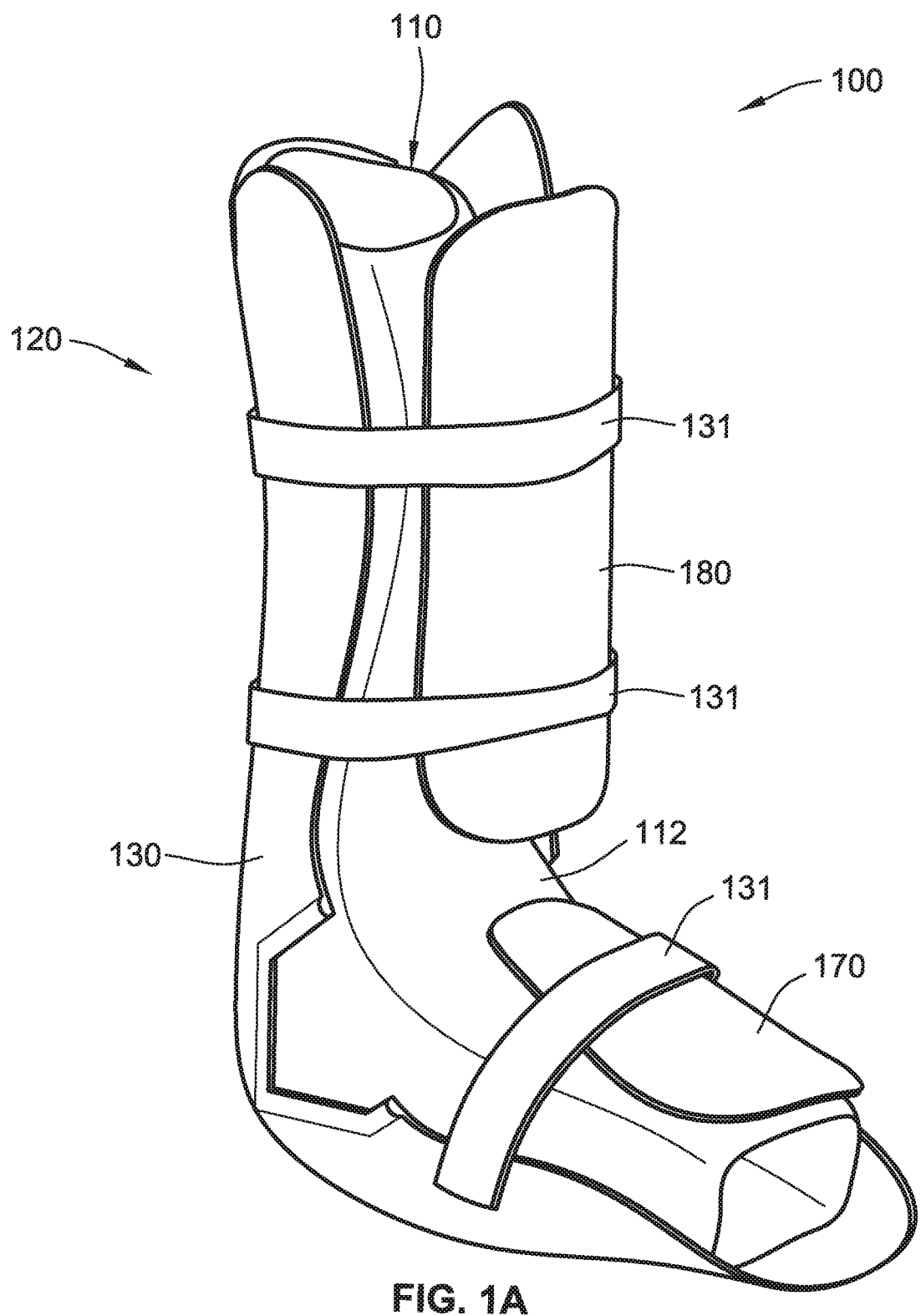
FIG. 1A is a perspective view of a walking boot according to some implementations of the present disclosure.

While the disclosure is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Figure 1B:
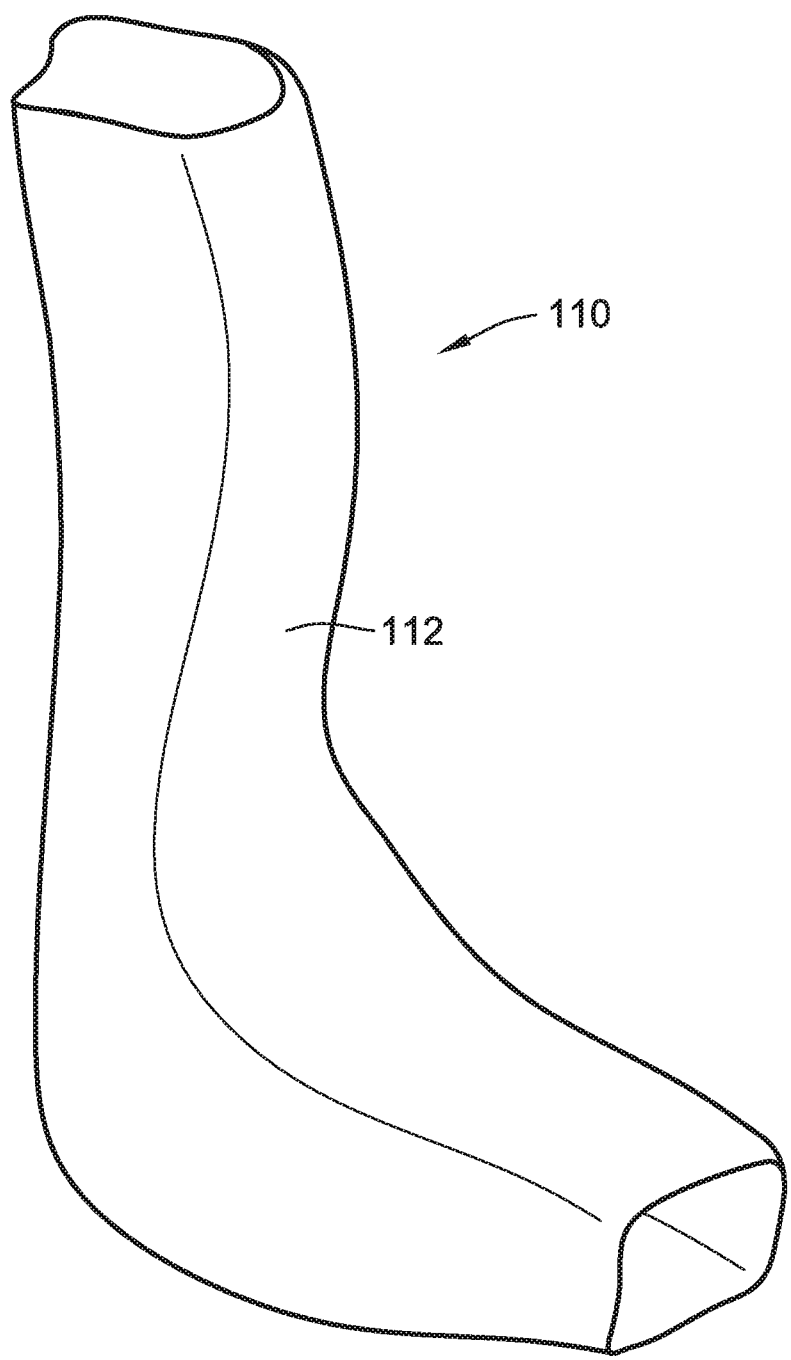
FIG. 1B is a perspective view of an inner fabric lining of the walking boot of FIG. 1A according to some implementations of the present disclosure.

Referring generally to FIGS. 1A and 1B, a walking boot 100 comprises an inner fabric lining 110 and a rigid outer shell 120. Generally, the walking boot 100 can be worn by a subject to immobilize an injury (e.g., an ankle injury, a foot injury, a leg injury, etc.) while permitting the subject to put weight on the injury (e.g., walk without the use of crutches). The walking boot 100 also aids in protecting the injury (e.g., an incision area from a surgical procedure) from further injury and/or aid in promoting healing of the injury while permitting the subject to put weight on the injury during the healing process.

As best shown in FIG. 1B, the inner fabric lining 110 of the walking boot 100 includes a plurality of fasteners 112 (e.g., hook and loop fasteners) to secure the inner fabric lining 110 to a portion of a foot, a portion of ankle, and a portion of a leg of a subject. The inner fabric lining 110 is generally used to support for and cushion the portion of a foot, the portion of ankle, and the portion of a leg of a subject. The inner fabric lining can also include an inflatable air bladder (not shown) that can be inflated with an external air pump (not shown) to improve the fit of the inner fabric lining 110 on a subject (e.g., such that the inner fabric lining 110 conforms to the portion of a foot, the portion of ankle, and the portion of a leg of a subject) and/or to compress or cushion an injury.

As shown in FIG. 1A, the rigid outer shell 120 includes a main body 130, a foot cover 170, and a shin cover 180. The rigid outer shell 120 is made from a rigid polymer material that resists bending/flexing when the walking boot 100 is worn by a subject. The rigid outer shell 120 can also include inner padding (not shown), such as a foam material, that provides additional support/stability for the wearer of the walking boot 100 and provides additional comfort/protection for the wearer of the walking boot 100. As described in further detail below, the rigid outer shell 120 receives a majority of the inner fabric lining 110 therein when the walking boot 100 is worn by a subject.

Figure 1C:
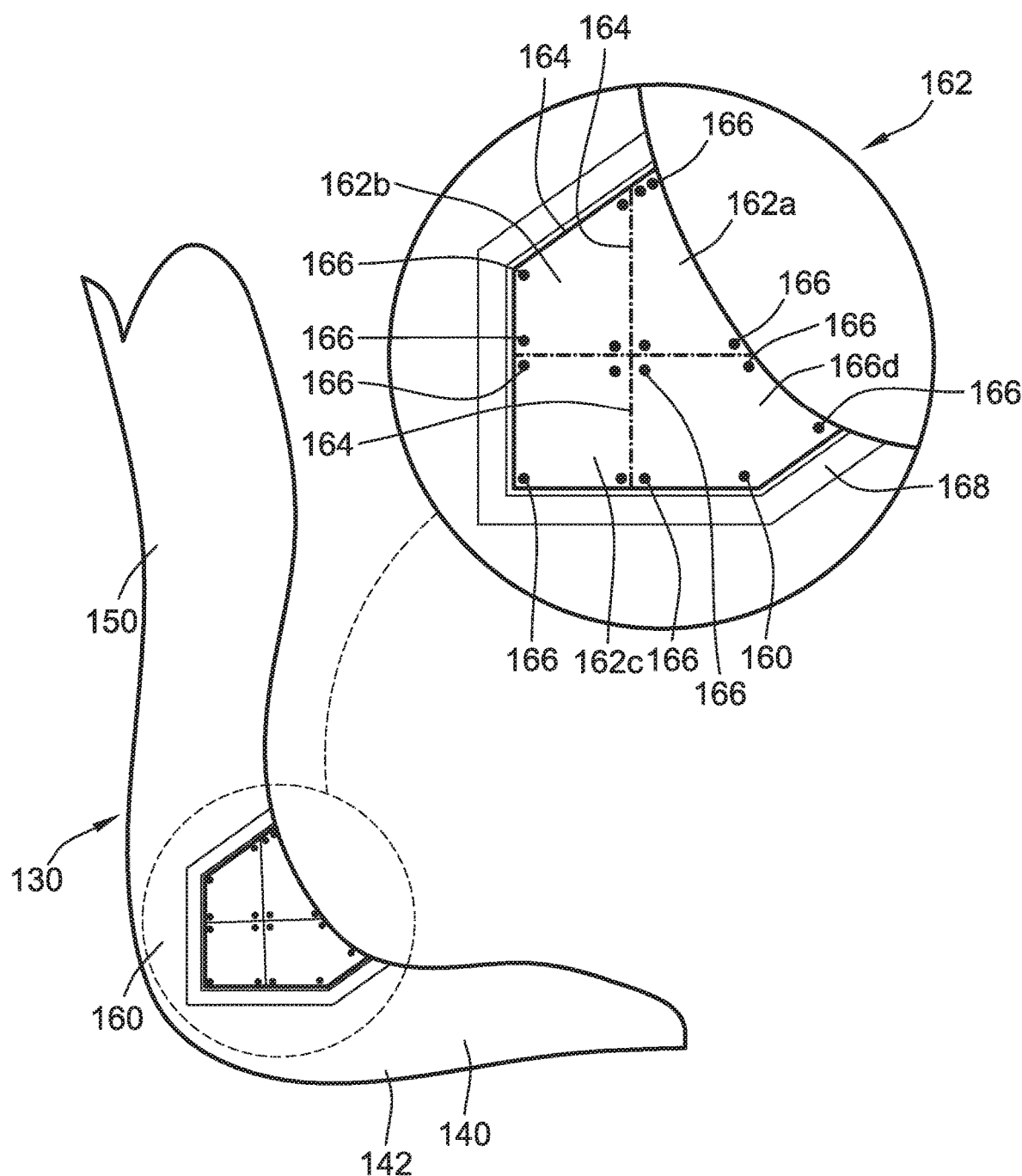
FIG. 1C is a side view of a main body of a rigid outer shell of the walking boot of FIG. 1A according to some implementations of the present disclosure.

Referring to FIGS. 1A and 1C, the main body 130 includes a plurality of fasteners 131 (FIG. 1A), a base portion 140, a leg portion 150, and an ankle support portion 160 (FIG. 1C). As described in further detail below, the main body 130 receives a portion of the inner fabric lining 110 (FIG. 1A) therein when the walking boot 100 is worn by a subject. The main body 130 includes a plurality of fasteners 131 (e.g., hook and loop fasteners) that couple the foot cover 170 and the shin cover 180 to the main body 130 to assemble the walking boot 100 (FIG. 1A).

As shown, the base portion 140, the leg portion 150, and the ankle support portion 160 are unitary and/or monolithic. The base portion 140, the leg portion 150, and the ankle support portion 160 of the main body 130 are coupled to one another such that the main body 130 has a general "L" shape (e.g., the base portion 140 is generally perpendicular to the leg portion 150). This "L" shape of the main body 130 of the rigid outer shell 120 aids in inhibiting pivoting/bending of an ankle of a wearer of the walking boot 100.

The base portion 140 receives a portion of the inner fabric lining 110 therein and supports a foot of a wearer of the walking boot 100. As best shown in FIG. 2, the base portion 140 includes an outer sole 142 that contacts the ground when a wearer of the walking boot 100 is walking. As shown, the outer sole 142 has a generally convex shape such that when the wearer of the walking boot 100 steps on the heel, the convex shape of the outer sole 142 of the base portion 140 urges the wearer to roll forward onto their toes. The outer sole 142 can include a plurality of treads (not shown) to aid in providing traction.

The leg portion 150 receives a portion of the inner fabric lining 110 therein and supports two opposing sides of a leg of a wearer of the walking boot 100. The leg portion 150 has a generally U-shaped profile such that the leg portion 150 at least partially surrounds two opposing sides of the leg of the wearer of the walking boot 100. The leg portion 150 can optionally include an air pump (not shown) that can be connected (e.g., using a tube) to the inflatable air bladder of the inner fabric lining 110 discussed above.

The ankle support portion 160 receives a portion of the inner fabric lining 110 therein and supports an ankle of the wearer of the walking boot 100 by at least partially surrounding two opposing sides of the ankle of the wearer. As best shown in FIG. 1C, the ankle support portion 160 includes a plurality of removable elements 162. As described in further detail below, removing at least one of the plurality of removable elements 162 from the ankle support portion 160 of the main body 130 of the rigid outer shell 120 aids in inhibiting contact between an incision area on a first side of the ankle of the wearer of the walking boot 100 and the rigid outer shell 120.

The plurality of removable elements 162 of the ankle support portion 160 includes a first removable element 162a, a second removable element 162b, a third removable element 162c, and a fourth removable element 162d, although other numbers of removable elements are possible (e.g., one removable element, three removable elements, six removable elements, ten removable elements, twenty removable elements, etc.). Each the plurality of removable elements 162 are defined by a plurality of fracturable score lines 164. As described in further detail below, the plurality of fracturable score lines 164 are lines of weakness that can be fractured (e.g., using a tool) to remove one or more of the plurality of removable elements 162 from the ankle support portion 160.

Each of the plurality of removable elements 162 optionally includes a plurality of force directors 166. As shown in FIG. 1C, each of the plurality of removable elements 162 includes one or more force directors 166 which are positioned adjacent to the corners of each of the plurality of removable elements 162. While each of the plurality of removable elements is shown as including four force directors 166, other numbers of force directors 166 per removable element 162 are possible (e.g., one force director, two force directors, six force directors, twelve force directors, etc.) Further, while the force directors 166 are positioned adjacent to corners of each of the plurality of removable elements 162, the plurality of force directors 166 can more generally be positioned anywhere on each of the plurality of removable elements 162 (e.g., adjacent to the corners of a removable element, in the center of a removable element, along the edges of the removable element adjacent to the fracturable score lines, or any combination thereof).

Figure 2B:
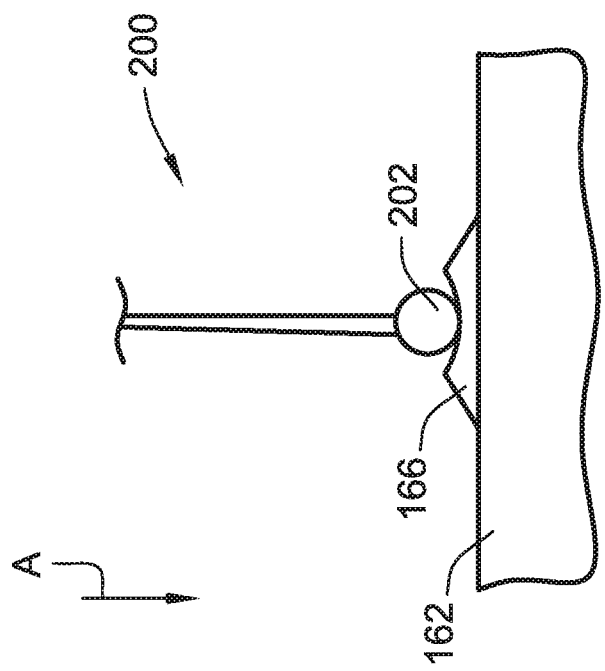
FIG. 2B is a side view of the force director of FIG. 2A and a tip of a removal tool according to some implementations of the present disclosure.
Figure 2A:
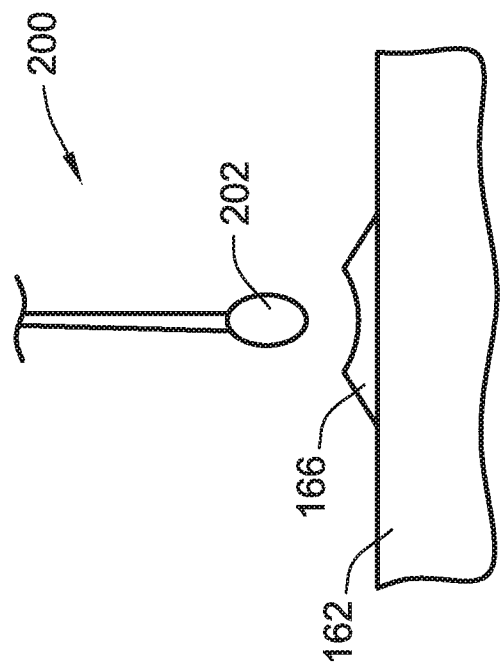
FIG. 2A is a side view of a force director of a removable element of the main body of FIG. 1C according to some implementations of the present disclosure.

Referring to FIGS. 2A and 2B, each of the plurality of force directors 166 is formed on an outer surface of the plurality of removable elements 162 and protrudes outwardly therefrom. Each of the plurality of force directors 166 has a generally concave profile for receiving a tip 202 of a removal tool 200 therein. As described in further detail below, placing the tip 202 of the removal tool 200 in one or more of the plurality of force directors 166 and moving (e.g., striking, hammering, etc.) the removal tool 200 in the direction of arrow A causes fracturing one or more of the plurality of score lines 164 defining one or more of the plurality of removable elements 162. The plurality of force directors 166 directs the force caused by movement (e.g., hammering) of the removal tool 200 to a concentrated area (e.g., an area that is smaller than if the tip 202 of the removal tool 200 were placed on the outer surface of one of the plurality of removable elements 162). Directing the force to this concentrated area aids in fracturing a desired one of the plurality of fracturable score lines 164 without breaking the ankle support portion 160 or fracturing other ones of the plurality of fracturable score lines 164.

In some implementations, the ankle support portion 160 includes a reinforcing portion 168 that surrounds the outermost ones the plurality of fracturable score lines 164. The reinforcing portion 160 can be made from the same material as the ankle support portion 160 or a different material (e.g., a metal material). The reinforcing portion 168 protrudes outwardly from an outer surface of the ankle support portion 160 to inhibit contact (e.g., direct or indirect contact) between the reinforcing portion and the wearer of the walking boot 100.

Figure 3:
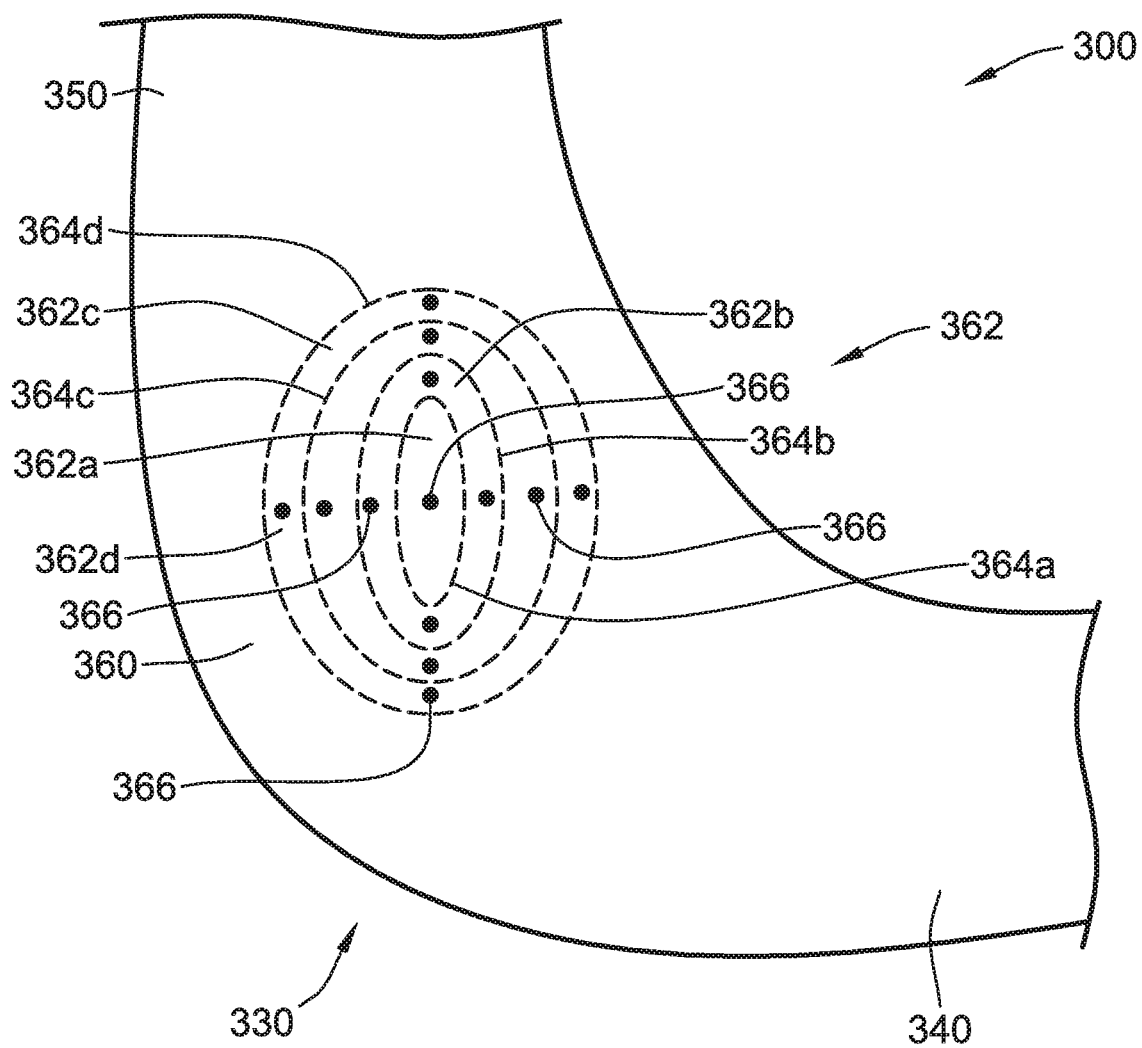
FIG. 3 is a partial side view of a main body of a rigid outer shell of a walking boot according to some implementations of the present disclosure.

Referring to FIG. 3, a walking boot 300 that is the same as, or similar to, the walking boot 100 (FIG. 1) described above includes a main body 330 that is similar to the main body 130. The main body 330 includes a base portion 340, a leg support portion 350, and an ankle support portion 360. The ankle support portion 360 includes a plurality of removable elements 362 that are similar to the plurality of removable elements 162 (FIG. 1C) in that removing at least one of the plurality of removable elements 362 from the ankle support portion 360 of the main body 330 aids in inhibiting contact between an incision area on a first side of the ankle of the wearer of the walking boot 300 and the main body 330.

The plurality of removable elements 362 includes a first removable element 362a, a second removable element 362b, a third removable element 362c, and a fourth removable element 362d. As shown, the plurality of removable elements 362 differ from the plurality of removable elements 162 (FIG. 1C) described above in that each of the plurality of removable elements 362 has a generally oval shape and are concentrically arranged such that each of the plurality of removable elements 362 has an outer perimeter (periphery) that is different than the others of the plurality of removable elements 362. More specifically, the fourth removable element 362d has an outer perimeter that is greater than the outer perimeter of the third removable element 362c, the third removable element 362c has an outer perimeter that is greater than the outer perimeter of the second removable element 362b, and the second removable element 362b has an outer perimeter that is greater than the outer perimeter of the first removable element 362a.

The ankle support portion 360 includes a plurality of fracturable score lines 364 that are similar to the fracturable score lines 164 (FIG. 1C) described above which define the plurality of removable elements 362. Further, each of the plurality of removable elements 362 includes a plurality of force directors 366 that are the same as, or similar to, the force directors 166 (FIGS. 2A and 2B) described above. The plurality of fracturable score lines 364 (FIG. 3) differ from the plurality of fracturable score lines 164 (FIG. 1C) in that a single fracturable score line defines each of the plurality removable elements 362. As shown, the plurality of fracturable score lines 364 includes a first fracturable score line 364a defining the first removable element 362a, a second fracturable score line 364b defining the second removable element 362b, a third fracturable score line 364c defining the third removable element 362c, and a fourth fracturable score line 364d defining the fourth removable element 362d. Thus, fracturing the one of the plurality of score lines 364 defining the outer perimeter (periphery) of a given removable element of the plurality of removable elements 362 causes the given removable element to be removed along with any of the plurality of removable elements 362 that have an outer perimeter (periphery) than the given removable element. For example, removal of the third removable element 362c by fracturing (e.g., using a tool) the third fracturable score line 364c causes the third removable element 362c to be removed along with the second removable element 362b and the first removable element 362a. In this manner, multiple removable elements of the plurality of removable elements 362 can be removed from the ankle support portion 360 by fracturing a single one of the plurality of fracturable score lines 364.

While each of the plurality of removable elements 362 are shown as being generally oval, other shapes are possible (e.g., generally rectangular, generally circular, etc.) Further, while the plurality of removable elements 362 is shown as including four removable elements, other numbers of removable elements are possible (e.g., one removable element, three removable elements, eighth removable elements, fifteen removable elements, etc.)

Figure 4A:
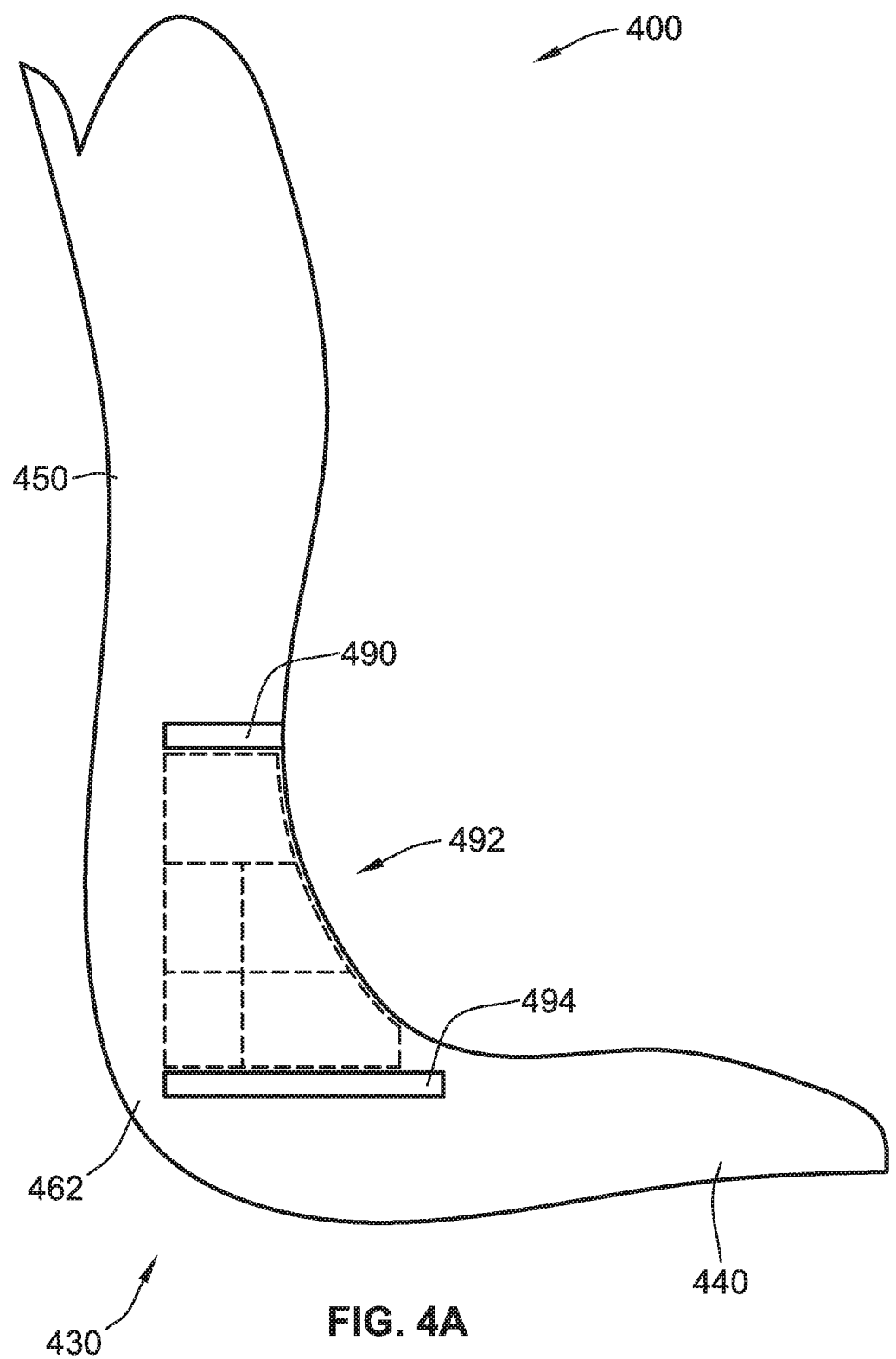
FIG. 4A is a side view of the main body of a rigid outer shell of a walking boot according to some implementations of the present disclosure.
Figure 4C:
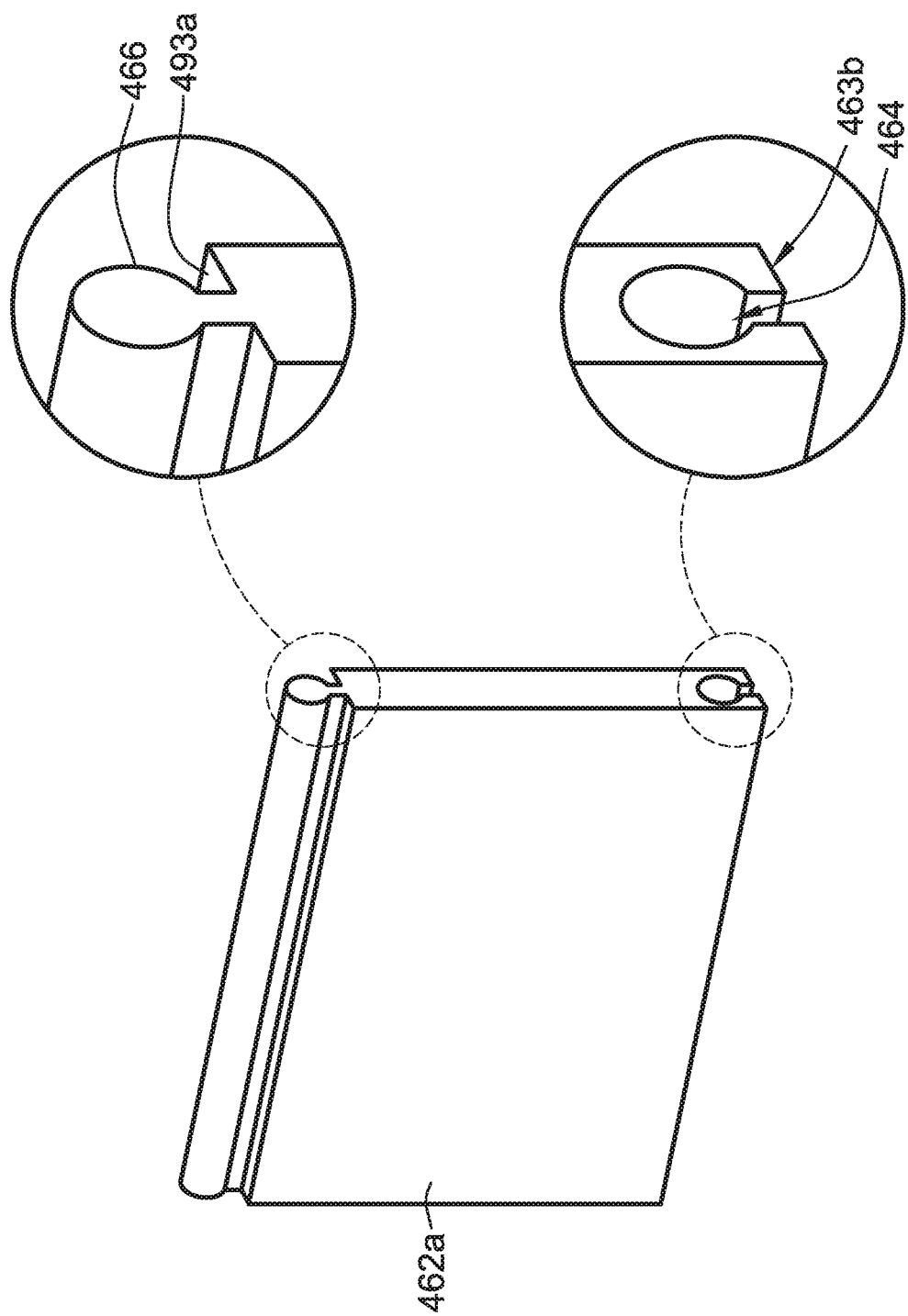
FIG. 4C is a perspective view of one of a plurality of removable elements of the main body of FIG. 4A according to some implementations of the present disclosure.

Referring generally to FIGS. 4A-4C, a walking boot 400 that is similar to the walking boot 100 (FIG. 1A) and the walking boot 300 (FIG. 3) described above includes a main body 430. The main body 430 is similar to the main body 130 (FIG. 1C) and the main body 330 (FIG. 3) in that the main body 430 includes a base portion 440, a leg support portion 450, and an ankle support portion 460. Like the ankle support portion 160 (FIG. 1C) and the ankle support portion 360 (FIG. 3), the ankle support portion 460 includes a plurality of removable elements 462 that can be selectively removed to aid in inhibiting contact (e.g., direct or indirect contact) between an incision area on an ankle of a wearer of the walking boot 400 and the main body 430 of the rigid outer shell.

The ankle support portion 460 differs from the ankle support portion 160 (FIG. 1C) and the ankle support portion 360 (FIG. 3) in that the ankle support portion 460 includes an upper track 490 and a lower track 494. As best shown in FIG. 4B, the upper track 490 includes a groove 492. As described in further detail below, the groove 492 is sized and shaped to receive (e.g., slidably engage) a tongue of one or more of the plurality of removable elements 462. The lower track 494 includes a tongue 496. As described in further detail below, the tongue 496 is sized and shaped to be received within (e.g., slidably engage) a groove of one or more of the plurality of removable elements 462. The upper track 490 is spaced from the lower track 494 to define an opening 498 in the ankle support portion 460 of the walking boot 400.

As best shown in FIG. 4C, each of the plurality of removable elements 462 includes a tongue and a groove. For example, a first removable element 462a of the plurality of removable elements 462 includes a groove 464 protruding from an upper surface and a tongue 466 formed on an opposing lower surface of the first removable element 462a. The tongue 466 is sized and shaped to be received within (e.g., slidably engage) the groove 492 of the upper track 490 and/or a groove of a different one(s) of the plurality of removable elements 462. Similarly, the groove 464 is sized and shaped to receive (e.g., slidably engage) the tongue 496 of the lower track 494 and/or a groove of a different one(s) of the plurality of removable elements 462. In this manner, each of the plurality of removable elements 462 can be removed from the ankle support portion 460 by sliding the removable element along the upper track 490, the lower track 494, or both. Advantageously, each of the plurality of removable elements 462 can reengage the upper track 490, lower track 494, or both after being removed. In contrast, each of the plurality of removable elements 162 (FIG. 1C) and the plurality of removable elements 362 (FIG. 3) cannot be put back into place after removal. Thus, the walking boot 400 can be reused for a different subject and/or a different injury. Further, in some implementations, certain ones of the plurality of removable elements 462 can be removed initially, and then added to fill a portion of the opening 498 as an incision area begins to heal (e.g., shrinks in size) to provide further structural support/stability as the wearer increases activities (e.g., walking) as the incision area heals.

While the plurality of removable elements 462 is shown as including five removable elements (FIG. 4A), other numbers of removable elements are possible (e.g., one removable element, four removable elements, eight removable elements, twenty removable elements, etc.) Further, while the upper track 490, lower track 494, and the plurality of removable elements 462 are shown as being formed on a first side of the main body 430 (i.e., such that the plurality of removable elements 462 are adjacent to one of two opposing sides of an ankle of a wearer of the walking boot 400), the upper track 490, lower track 494, and the plurality of removable elements 462 can be reversed and formed on a second side of the main body 430. Alternatively, a second upper track, a second lower track, and a second plurality of removable elements (not shown) can be formed on the second side of the main body 430 (i.e., such that the plurality of removable elements 462 is adjacent to a first side of an ankle of a wearer and the second plurality of removable elements is adjacent to a second, opposing side of the ankle of the wearer).

Referring to FIG. 5A, a method 500 for making a walking boot (e.g., the walking boot 100, the walking boot 300, or the walking boot 400) includes a first step 510, a second step 520, a third step 530, and a fourth step 540.

The first step 510 includes identifying an area of the ankle support portion of the main body of the rigid outer shell of the walking boot that is directly adjacent to an incision area on a first side of an ankle of a subject. For example, referring to FIG. 5B, the first step 510 can include identifying a target area 512 of the ankle support portion 160 of the main body 130 of the rigid outer shell 120 of the walking boot 100 (FIGS. 1A and 1C). As described above, the ankle support portion 160 at least partially surrounds and supports two opposing sides of the ankle of the subject when wearing the walking boot 100. Contact (e.g., pressure, rubbing, etc.) between the rigid outer shell 120 and the incision area on the ankle of the subject while wearing the walking boot 100 is undesirable as such contact can cause the subject pain/discomfort (e.g., while walking) and/or slow the healing of the incision area. The undesirable contact may be direct contact between the incision area and the rigid outer shell 120 or indirect contact between the incision area and the rigid outer shell 120 (e.g., contact through one or more layers, such as the inner fabric lining 110 (FIG. 1A)).

To identify the target area 512 during the first step 510, a user (e.g., a physician, a physician's assistant, a nurse, or the like) can place the main body 130 of the rigid outer shell 120 on the foot, ankle, and/or leg of the subject and identify the target area 512 by directly inspecting which area of the ankle support portion 160 is directly adjacent to the incision area on the ankle. The subject may provide feedback to the user to aid in identifying the target area 512. Alternatively, the user can measure the location of the incision area on the ankle of the subject and use this measurement to identify the target area 512 on the ankle support portion 160 without having to place the main body 130 of the rigid outer shell 120 on the subject, which may cause pain/discomfort and requires the presence of the subject.

In some implementations, the identified target area 512 is larger than the incision area on the ankle of the subject (e.g., 110% of the incision area, 125% of the incision area, 150% of the incision area, 200% of the incision area etc.) to aid in inhibiting contact (e.g., direct contact or indirect contact) and allowing for variations in the position of the incision area on the ankle relative to the ankle support portion 160, for example, while the subject is walking.

Figure 5B:
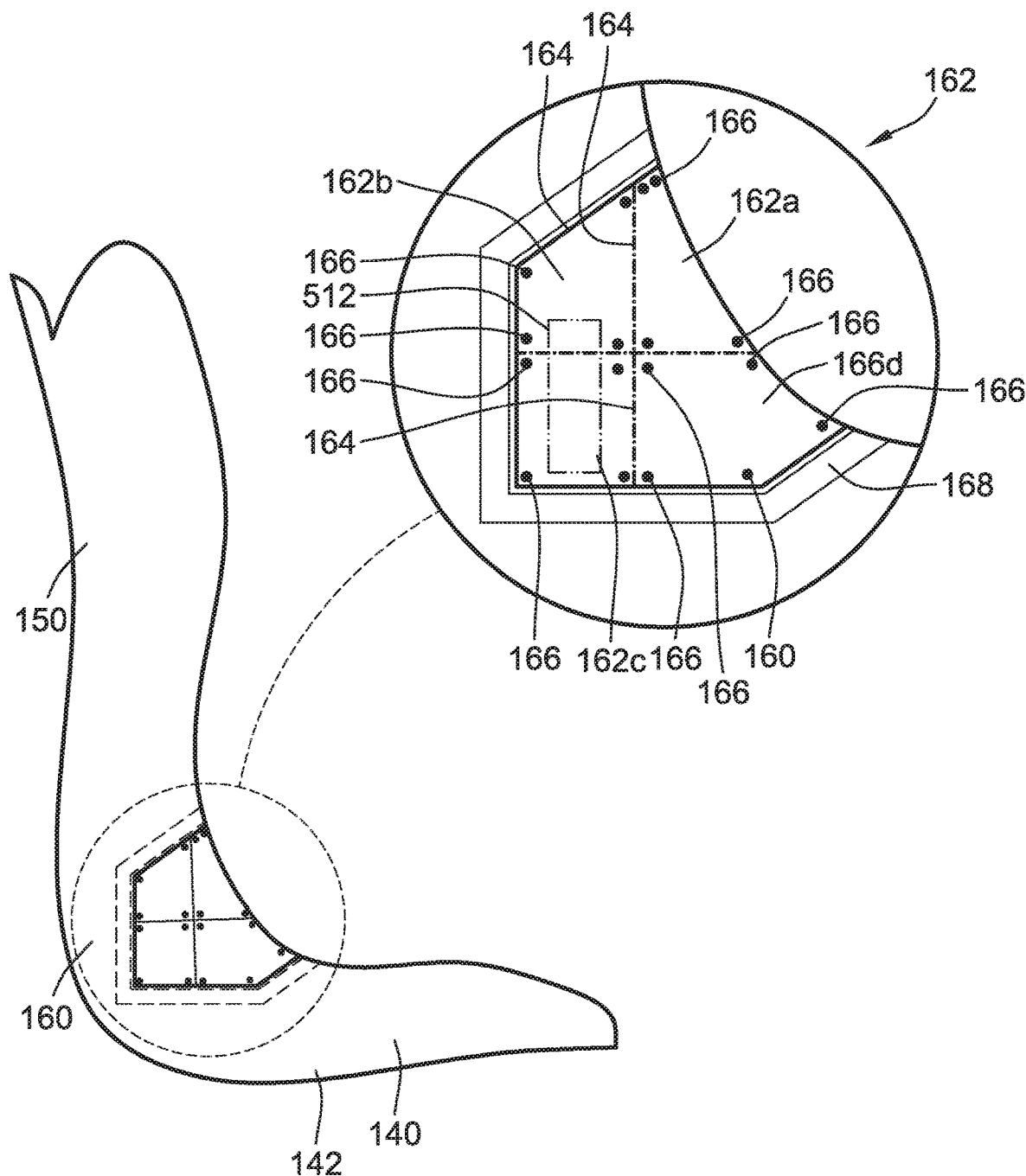
FIG. 5B is a partial side view of a target area and a plurality of removable elements of an ankle support portion of the walking boot of FIG. 3 according to some implementations of the present disclosure.

After identifying the target area 512 during the first step 510, the user then selects one or more of the removable elements of the ankle support portion that are at least partially positioned within the target area 512. For example, as shown in FIG. 5B, a portion of the second removable element 162b and a portion the third removable element 462c are positioned within the target area 512 identified during the first step 510. During the second step 520, the user selects the second removable element 162b, and the third removable element 162c for removal during the third step 530 described below.

Figure 5C:
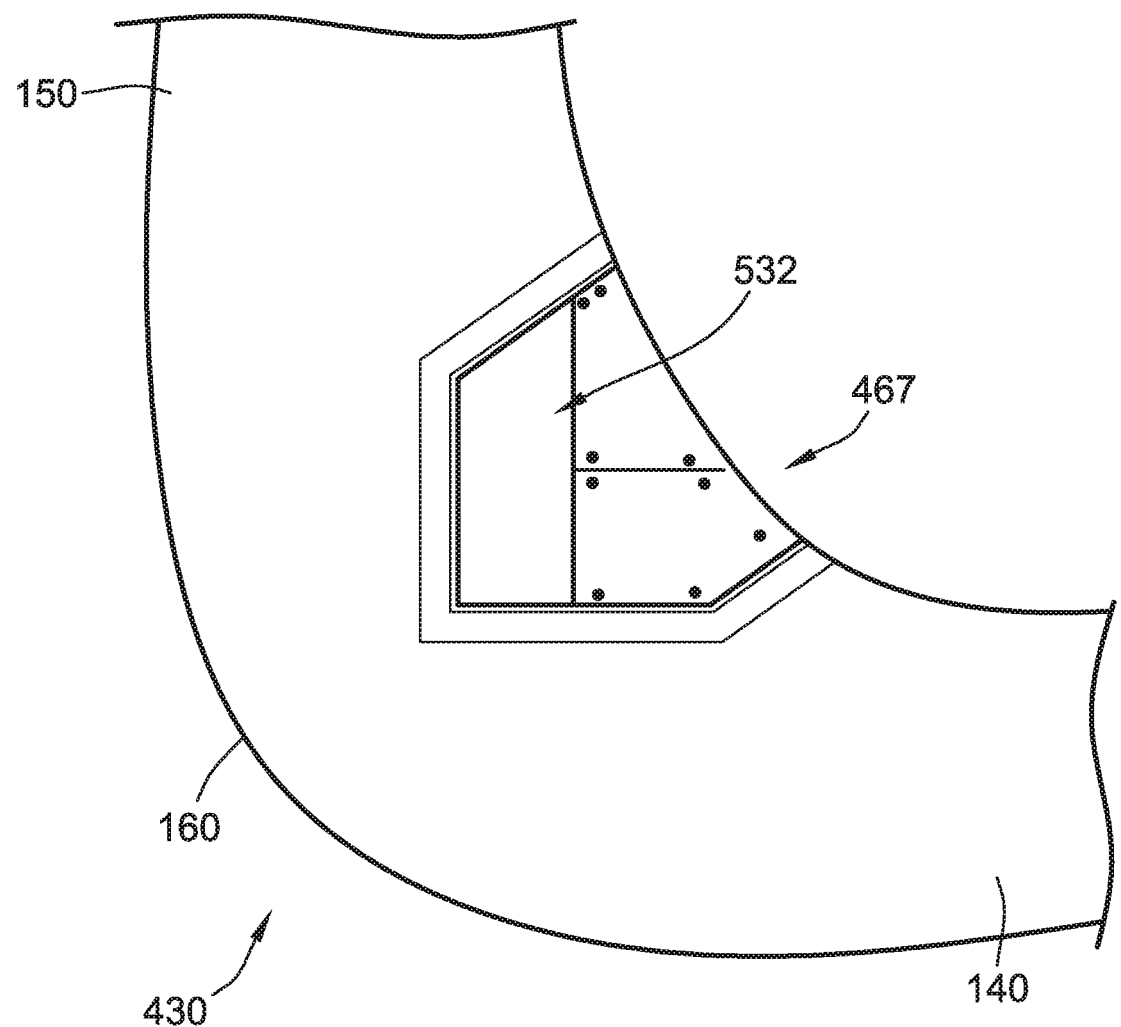
FIG. 5C is a partial side view of the ankle support portion of the walking boot of FIG. 3 with a plurality of removable elements removed according to some implementations of the present disclosure.

The third step 530 includes removing the one or more selected removable elements from the second step 520. As shown in FIG. 5C, the second removable element 162b and the third removable element 162c, which were selected during the second step 520, are removed from the ankle support portion 160, thereby defining an opening 532 in the ankle support portion 160. The one or more selected removable elements (second step 520) can be removed by, for example, by placing the removal tool 200 (FIGS. 2A and 2B) described above in a group of the plurality of force directors 166 and applying a force (e.g., by striking the removal tool 200 with a hammer) to cause the removal tool 200 to fracture a group of the plurality of fracturable score lines 164 defining the periphery of the second removable element 162b and the third removable element 162c. Alternatively, the one or more selected removable elements (second step 520) can be removed in the third step 530 by cutting (e.g., using a knife, a saw, or the like) one or more of the fracturable score lines 164. In other implementations, one or more of the fracturable score lines 164 can be fractured using a stamp (not shown) that acts like a cookie-cutter to remove the one or more selected removable elements.

During the optional fourth step 540, the user or the subject then places the walking boot 100 (FIG. 1A) on the subject. To do so, the user or the subject places the inner fabric lining 110 (FIG. 1B) on at least a portion of the foot, the ankle, and the leg of the subject and secures the inner fabric lining 110 to the subject using the plurality of fasteners 112. The user or the subject then places the inner fabric lining 110 in the main body 130 of the rigid outer shell 120 (FIG. 1C) such that the base portion 140 supports the foot of the subject, the leg portion 150 supports the leg of the subject, and the ankle support portion 160 supports the ankle of the subject. The user or the subject then completes the assembly of the walking boot 100 (FIG. 1A) by placing the shin cover 180 and the foot cover 170 on a front surface of the inner fabric lining 110 and securing the shin cover 180 and the foot cover 170 to the main body 130 using the plurality of fasteners 131 (FIG. 1A).

If the subject reports any undesirable contact (e.g., direct or indirect) between the rigid outer shell 120 and the incision area (e.g., while walking in the walking boot 100) to the user after the fourth step 540, the method 500 can further include disassembling the walking boot 100 and repeating the first step 510, the second step 520, the third step 530, and the fourth step 540 one or more times until the subject reports that there is no contact (e.g., direct or indirect) between the rigid outer shell 120 and the incision area on the ankle.

Advantageously, the method 500 permits a user to customize the walking boot 100 as needed for a given subject to inhibit or prevent contact (e.g., direct or indirect) between the rigid outer shell 120 and the incision area on the ankle of the subject. Physicians often have a limited supply of walking boots and thus it is advantageous that the walking boot 100 can be adapted to any subject rather than requiring a custom-made walking boot for each subject. In many cases a subject may require a walking boot but does not have an incision area that requires the removal of one or more removable elements to inhibit contact with the rigid outer shell 120. A physician can provide the walking boot 100 to a variety of subjects, such as, for example, a subject that has an injury but no incision area, a subject with a large incision area, a subject with a small incision area, a subject with multiple incision area, etc.

By requiring a tool (e.g., the removal tool 200, a cutting tool, a stamp, etc.) during the fourth step 540, the method 500 limits the ability of the subject to remove (unintentionally or intentionally) other ones of the plurality of removable elements 162 other than those selected during the second step 520. This is advantageous because removing all of the removable elements of the plurality of removable elements 162 from the ankle support portion 160 could cause the walking boot 100 to fail during use by the wearer (e.g., if the wearer is overweight). Thus, a physician can selectively remove only the ones of the plurality of removable elements 162 that are necessary to inhibit contact with an incision area while ensuring that the other ones of the plurality of removable elements 162 remain in place to provide the required support/stability.

While the method 500 has been described and shown in FIGS. 5B and 5C being used to make the walking boot 100, the method 500 can more generally be used to make the walking boot 300, the walking boot 400, or other similar walking boots. In such implementations, the removal of the selected removable elements during third step 530 may differ depending on the configuration of the walking boot (e.g., sliding the selected removable elements along the upper track 490 and the lower track 494 in the case of walking boot 400).

Figure 6:
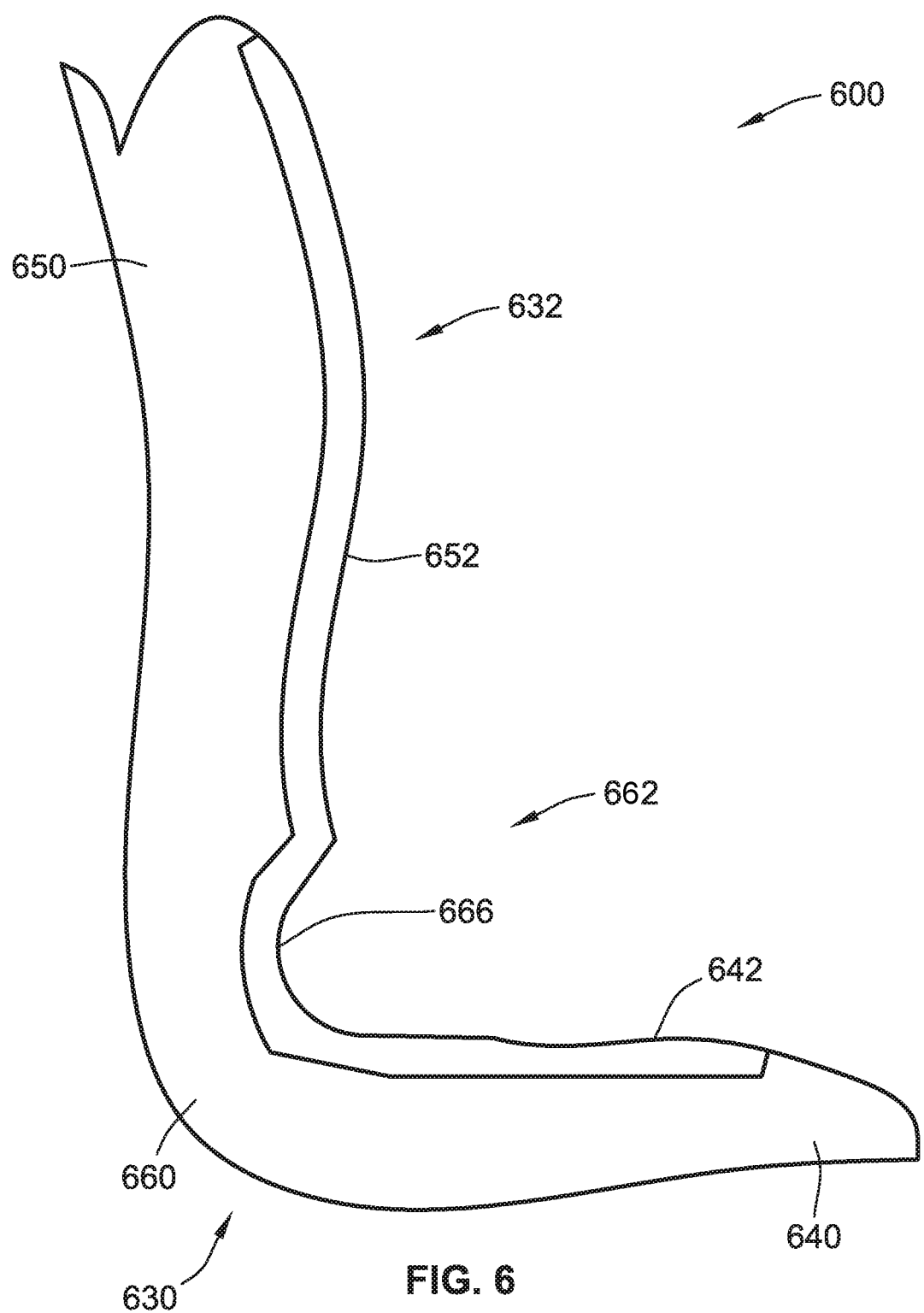
FIG. 6 is a side view of a main body of a rigid outer shell of a walking boot according to some implementations of the present disclosure.

Referring to FIG. 6, a walking boot 600 that is similar to the walking boots 100, 300, and 400 described above includes a main body 630 of a rigid outer shell. The main body 630 (FIG. 6) is similar to the main body 130 (FIG. 1C) in that the main body 630 includes a base portion 640, a leg support portion 650, and an ankle support portion 660. The main body 630 (FIG. 6) differs from the main body 130 (FIG. 1C) in that the main body 630 includes a reinforcing member 632. Further, the ankle support portion 660 differs from the ankle support portion 160 (FIG. 1C) in that the ankle support portion 660 includes an opening 662.

As best shown in FIG. 6, the opening 662 has a general "C" or semi-circular shape. Like the opening 532 (FIG. 5C), which is formed when one or more removable elements are removed from the ankle support portion 160 as described above, the opening 662 aids in inhibiting contact (e.g., direct contact or indirect contact) between incision area(s) on one (or both) of two opposing sides of an ankle of a subject and the main body 630 of the rigid outer shell. In other words, the opening 662 of the ankle support portion 660 is positioned such that incision area(s) on the ankle of the subject are positioned within the opening 662 when the walking boot is worn by a subject.

As described above, the walking boots described herein after used to immobilize an injury and permit a subject to put weight on the injury. Including the opening 662 in the ankle support portion 660 of the walking boot 600 reduces the maximum stress that the main body 630 can accommodate without failing (e.g., compared to the walking boot 100). The reinforcing member 632 is coupled to the main body 630 to provide structural support and stability such that the main body 630 can accommodate the same maximum stress as a main body without the opening 662 (e.g., the walking boot 100). The reinforcing member 632 can be made from a polymer material (e.g., the same material as the main body 630) and can be unitary and/or monolithic with the main body 630. Alternatively, in some implementations, the reinforcing member 632 is made from a metal material and is coupled to the main body 630 (e.g., using an adhesive, one or more clips that are integrally formed with the main body 630, or the like, or any combination thereof).

The reinforcing member 632 includes a first segment 642 coupled to the base portion 640 of the main body 630 and a second segment 652 coupled to the leg portion 650 of the main body. The first reinforcing member 632 also includes a third segment 666 coupled to the ankle support portion 660. As shown, the third segment 666 couples the first segment 642 and the second segment 652 together and has a general "C" or semi-circular shape such that the third segment 666 partially surrounds the opening 662.

Advantageously, the reinforcing member 632 allows the walking boot 600 to accommodate the same or similar stresses as a main body without an opening (e.g., the main body 130) without requiring the steps of identifying a target area, selecting removable elements, and removing the selected removable elements (e.g., as described in reference to the method 500). Thus, the walking boot 600 can be worn by a subject (e.g., a subject with multiple incision areas on one side of the ankle, a subject with an incision area(s) on both sides of the ankle, a subject without any incision areas, etc.) without any further modifications or steps.

While the opening 662 and the reinforcing member 632 are shown on one side of the walking boot 600 (e.g., such that the opening 662 is adjacent to one of two opposing sides of an ankle of a wearer of the walking boot 600), the walking boot 600 can include a second opening (not shown) that is the same as the opening 662 and a second reinforcing member (not shown) that is the same as the reinforcing member 632 such that the first opening 662 is adjacent to a first side of an ankle of a wearer of the walking boot 600 and the second opening is adjacent to an opposing second side of an ankle of a wearer of the walking boot 600.

Figure 7A:
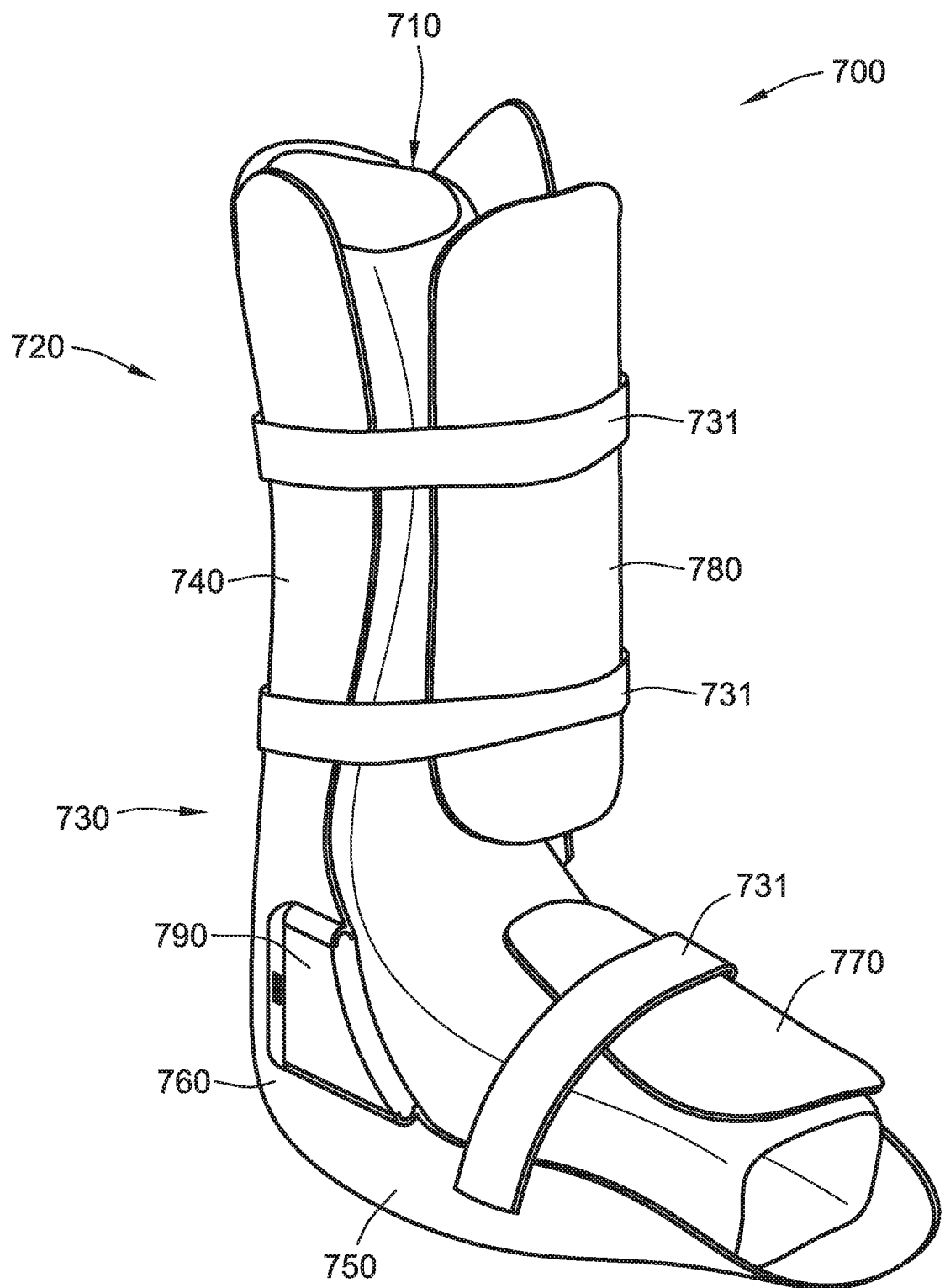
FIG. 7A is a perspective view of a walking boot according to some implementations of the present disclosure.
Figure 7B:
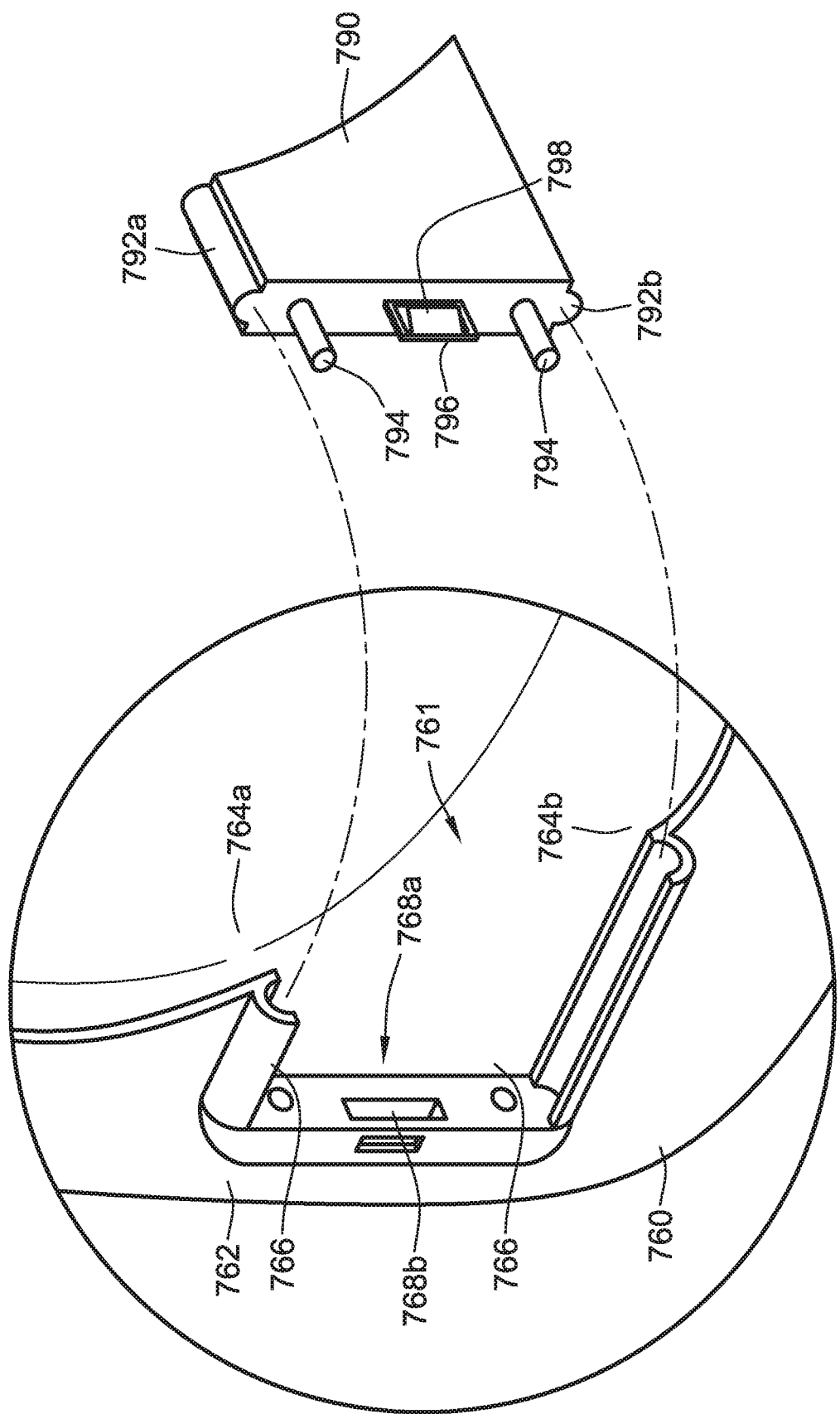
FIG. 7B is a partial side view of an ankle support portion of the walking boot of FIG. 7A according to some implementations of the present disclosure.

Referring to FIGS. 7A and 7B, a walking 700 that is similar to the walking boots 100, 300, 400, 600 described herein includes an inner fabric lining 710 and a rigid outer shell 720. The rigid outer shell 720 includes a main body 730, a foot cover 770, and a shin cover 780. The main body 730 also includes a plurality of fasteners 731 (e.g., hook and loop fasteners) that couple the foot cover 770 and the shin cover 780 to the main body 730 to assemble the walking boot 700.

The main body 720 includes a base portion 740, a leg portion 750, and an ankle support portion 760. As best shown in FIG. 7B, the ankle support portion 760 differs from the other ankle support portions described herein in that the ankle support portion 760 includes an opening 761, a bulged portion 762, and a removable element 790 removably disposed within the opening 761.

As shown in FIG. 7B, the removable element 790 includes an upper tongue 792a, a lower opposing tongue 792b, a plurality of posts 794, and a clasp 796. The removable element 790 is sized and shaped such that the removable element 790 generally fills the opening 761 of the ankle support portion 760 when the removable element is coupled to the ankle support portion 760. The upper tongue 792a and the lower tongue 792b define the opening 761 and each have a general u-shape, although other shapes are contemplated (e.g., rectangular, triangular, polygonal, etc.) As described in further detail herein, the upper tongue 792a and the lower tongue 792b aid in removable coupling the removable element 790 to the bulged portion 762 of the ankle support portion 760.

Each of the plurality of posts 794 of the removable portion extends from an outer surface of the removable element 790 and have a generally cylindrical shape, although other shapes and sizes are contemplated (e.g., rectangular, triangular, polygonal, etc.) While the plurality of posts 794 is shown as including two posts, more generally, the plurality of posts 794 can include any suitable number of posts (e.g., one post, three posts, five posts, etc.) As described in further detail herein, the plurality of posts 794 of the removable element 790 aid in removably coupling the removable element 790 to the bulged portion 762 of the ankle support portion 720.

The clasp 796 is positioned between two of the plurality of posts 794 and extends from an outer surface of the removable element 790. The clasp 796 includes a deflectable tongue 798 that is unitary and/or monolithic with the clasp 796. The deflectable tongue 798 is configured to at least partially defect responsive to application of a force and is generally biased towards the position shown in FIG. 7B. As described in further detail herein, the clasp 796 and the deflectable tongue 798 thereof aid in removable coupling the removable element 790 to the bulged portion 762 of the ankle support portion 760. While the removable element 790 is shown as including both the plurality of posts 794 and the clasp 796, in some implementations, the removable element 790 includes just the plurality of posts 794 or just the clasp 796.

The bulged portion 762 is unitary and/or monolithic with the ankle support portion 760 and extends outwardly in a direction away from the ankle of the subject when the walking boot 700 is worn. The bulged portion 762 includes an upper track 764a, an opposing lower track 764b, a plurality of sockets 766, a hollow clasp housing 768a, and a clasp tongue aperture 768b. The upper track 764a and the lower track 764b are sized and shaped (e.g., with a generally u-shape) to correspond to the shape of the upper tongue 792a and the lower opposing tongue 792b of the removable element 790 such that the upper track 764a and the lower track 764b can receive the upper tongue 792a and the lower opposing tongue 792b, respectively, to aid in removable coupling the removable element 790 to the ankle support portion 760.

While the bulged portion 762 is shown as including both the upper track 764a and the lower track 764b (e.g., female connectors) to receive portions of the upper tongue 792a and the lower tongue 792a (e.g., male connectors) of the removable element 790 therein, in other implementations, the bulged portion 762 and the removable element 790 can include any combination of male and/or female connectors (e.g., the bulged portion 764 includes one track for receiving a tongue of the removable element 790 and the bulged portion 764 includes one tongue that is received by a track of the removable element 790.

The plurality of sockets 766 of the bulged portion 762 are sized, shaped, and positioned to receive the plurality of posts 794 of the removable element 790 therein. Disposing the plurality of posts 794 into the plurality of sockets 766 creates an interference or press fit that aids in removably coupling the removable element 790 to the bulged portion 762 of the ankle support portion 760.

Similarly, the hollow clasp housing 768a is sized, shaped, and positioned to receive the clasp 796 of the removable element 790 therein. Disposing the clasp 796 of the removable element 790 within the hollow clasp housing 768a aids in removably coupling the removable element 790 to the bulged portion 762. More specifically, as the clasp 796 is initially disposed within the hollow clasp housing 768a, the deflectable clasp tongue 798 deflects to permit the clasp 796 to move within the hollow clasp housing 768a. As the clasp 796 continues to be inserted into the hollow clasp housing 768a, the deflectable clasp tongue 798 engages the clasp tongue aperture 768b that is sized and shaped to receive the deflectable clasp tongue 798 therein such that a portion of the delectable clasp tongue 798 protrudes from the clasp tongue aperture 768*b*. This engagement of the deflectable clasp tongue 798 and the clasp tongue aperture 768*b* further aids in removably coupling the removable element 790 to the bulged portion 762. To remove the clasp 798 from the hollow clasp housing 768*a*, a force is applied to the deflectable clasp tongue 798 (e.g., a user presses the portion of the deflectable clasp tongue 798 protruding from the bulged portion 762) to deflect the deflectable clasp tongue 798 and permit the clasp 796 to be removed.

While the walking boot 700 is shown and described herein as included one removable element 790 on a first side of the ankle support portion 760, in some implementations, the walking boot 700 includes a second removable portion (not shown) that is the same as, or similar to, the removable portion 790 that that is positioned on a second opposing side of the walking boot 700. In such implementations, the second removable portion is coupled to the walking boot 700 in the same or similar manner as the removable portion 790 described herein.

It is to be understood that many modifications and variations may be devised given the above description of the general principles of the present disclosure. It is intended that all such modifications and variations be considered as within the spirit and scope of the present disclosure, as defined in the following claims.

What is claimed is:

1. A boot comprising:
   a rigid outer shell including a main body having: a base portion configured to be positioned adjacent to a portion of a foot of a subject;
   a leg portion configured to be positioned adjacent to a portion of a leg of the subject; and
   an ankle support portion that couples the base portion of the main body to the leg portion of the main body, the ankle portion of the main body being configured to be positioned adjacent to two opposing sides of an ankle of the subject, the ankle support portion of the main body having one or more removable elements, a first track including a groove, and an opposing second track including a tongue and being spaced from the first track to define an opening in the ankle support portion, each of the one or more removable elements including a tongue on a first edge and a groove on a second edge,
   wherein the tongue of each of the one or more removable elements is configured to slidably engage to the groove of the first track, or to the groove of another one of the one or more removable elements,
   wherein a first one of the one or more removable elements, being configured to be positioned adjacent to a first one of the two opposing sides of the ankle, is configured to be removed from the rigid outer shell to aid in preventing contact between an incision area on the first side of the ankle of the subject and the rigid outer shell.

2. The boot of claim 1, wherein the ankle support portion of the main body of the rigid outer shell includes a plurality of fracturable score lines defining the one or more removable elements, wherein selectively fracturing the plurality of fracturable score lines causes at least one of the one or more removable element to be removed from the ankle support portion.

3. The boot of claim 2, wherein the plurality of fracturable score lines are concentrically arranged such that a second one of the one or more removable elements defined by a second group of the plurality of fracturable score lines is larger than a first one of the one or more removable elements defined by a first group of the plurality of fracturable score lines.

4. The boot of claim 2, wherein each of the one or more removable elements includes a plurality of stress directors configured to (i) receive a portion of a removal tool therein and (ii) aid in fracturing a group of the plurality of fracturable score lines to remove at least one of the one or more removable elements using the removal tool.

5. The boot of claim 3, wherein each of the one or more removable elements defined by the plurality of fracturable score lines have a generally circular shape.

6. The boot of claim 1, wherein the ankle portion of the main body of the rigid outer shell includes a reinforcing portion adjacent to the one or more removable elements, wherein the reinforcing portion protrudes outwardly from an outer surface of the ankle portion.

7. The boot of claim 1, further comprising an inner fabric lining including one or more fasteners configured to secure the inner fabric lining to the portion of the foot, the portion of the ankle, and the portion of the leg of the subject, and the rigid outer shell being configured to receive a majority of the inner fabric lining therein.

8. The boot of claim 1, wherein the rigid outer shell includes a foot cover and a shin cover, the foot cover being coupled to the main body via one or more fasteners and the shin cover being coupled to the main body via one or more fasteners.

9. A boot comprising:
   a rigid outer shell including a main body having:
      a base portion configured to support a portion of a foot of a subject;
      a leg portion configured to support a portion of a leg of the subject; and
      an ankle support portion integral with and coupling the base portion of the main body with the leg portion of the main body, the ankle portion of the main body being configured to support two opposing sides of an ankle of the subject, the ankle support portion including (i) an opening, (ii) a removable element disposed within the opening, and (iii) a bulged portion configured to receive an attachment member of the removable element at least partially therein such that responsive to the removable element being positioned within the opening, the removable element is removably coupled to the bulged portion, the attachment member of the removable element including a clasp and the bulged portion including a hollow clasp housing being configured to slidably receive the clasp of the attachment member therein to aid in coupling the removable element to the bulged portion,
      wherein responsive to the removable element being removed from the opening, the opening in the ankle support portion aids in preventing contact between an incision area on a first of the two opposing sides of the ankle of the subject and the rigid outer shell.

10. The boot of claim 9, wherein the hollow clasp housing of the bulged portion includes a tongue aperture and the clasp of the attachment member includes a deflectable tongue configured to engage the tongue aperture of the hollow clasp housing to aid in removably coupling the removable element to the bulged portion.

11. The boot of claim 9, wherein the bulged portion is an outwardly extending bulged portion that only extends in a direction away from the ankle of the subject.

12. The boot of claim 9, further comprising an inner fabric lining including one or more fasteners configured to secure the inner fabric lining to the portion of the foot, the portion of the ankle, and the portion of the leg of the subject, and the rigid outer shell being configured to receive a majority of the inner fabric lining therein.

13. The boot of claim 9, wherein the rigid outer shell includes a foot cover and a shin cover, the foot cover being coupled to the main body via one or more fasteners and the shin cover being coupled to the main body via one or more fasteners.

14. A boot comprising:
a rigid outer shell including a main body having:
a base portion configured to support a portion of a foot of a subject;
a leg portion configured to support a portion of a leg of the subject;
an ankle support portion integral with and coupling the base portion of the main body with the leg portion of the main body, the ankle portion of the main body being configured to support two opposing sides of an ankle of the subject, the ankle support portion including (i) an opening, (ii) a removable element disposed within the opening, and (iii) a bulged portion configured to receive an attachment member of the removable element at least partially therein such that responsive to the removable element being position within the opening, the removable element is removably coupled to the bulged portion, the attachment member of the removable element including one or more posts and the bulged portion including one or more corresponding sockets, each of the one or more corresponding sockets being configured to receive a corresponding one of the one or more posts of the attachment member therein to aid in coupling the removable element to the bulged portion,
wherein responsive to the removable element being removed from the opening, the opening in the ankle support portion aids in preventing contact between an incision area on a first of the two opposing sides of the ankle of the subject and the rigid outer shell.

15. The boot of claim 14, wherein the one or more posts are configured to be press fit into the one or more corresponding sockets of the bulged portion.

16. The boot of claim 15, wherein a lower edge of the opening in the ankle support portion includes a groove and a corresponding lower edge of the removable element includes a tongue configured to engage the groove of the lower edge of the opening in the ankle support portion.

17. A boot comprising: a rigid outer shell including a main body having: a base portion configured to support a portion of a foot of a subject;
a leg portion configured to support a portion of a leg of the subject; and an ankle support portion integral with and coupling the base portion of the main body with the leg portion of the main body, the ankle portion of the main body being configured to support two opposing sides of an ankle of the subject, the ankle support portion including an opening, a removable element disposed within the opening, and a bulged portion configured to receive an attachment member of the removable element at least partially therein such that responsive to the removable element being position within the opening, the removable element is removably coupled to the bulged portion,
wherein an upper edge of the opening in the ankle support portion includes a first groove or a first tongue and a corresponding upper edge of the removable element includes a second tongue configured to engage the first groove of the upper edge of the opening in the ankle support portion or a second groove configured to engage the first tongue of the upper edge of the opening in the ankle support portion such that the removable element is slidably disposed within the opening,
wherein responsive to the removable element being removed from the opening, the opening in the ankle support portion aids in preventing contact between an incision area on a first of the two opposing sides of the ankle of the subject and the rigid outer shell.

18. The boot of claim 17, further comprising an inner fabric lining including one or more fasteners configured to secure the inner fabric lining to the portion of the foot, the portion of the ankle, and the portion of the leg of the subject, and the rigid outer shell being configured to receive a majority of the inner fabric lining therein.

19. The boot of claim 17, wherein the rigid outer shell includes a foot cover and a shin cover, the foot cover being coupled to the main body via one or more fasteners and the shin cover being coupled to the main body via one or more fasteners.

* * * * *